(12) United States Patent
Frey

(10) Patent No.: US 7,208,651 B2
(45) Date of Patent: Apr. 24, 2007

(54) PRODUCT RECOVERY FROM SIMULATED-MOVING-BED ADSORPTION

(75) Inventor: Stanley J. Frey, Palatine, IL (US)

(73) Assignee: UOP LLC, Des Plaines, IL (US)

( * ) Notice: Subject to any disclaimer, the term of this patent is extended or adjusted under 35 U.S.C. 154(b) by 225 days.

(21) Appl. No.: 11/072,883

(22) Filed: Mar. 3, 2005

(65) Prior Publication Data

US 2006/0199989 A1 Sep. 7, 2006

(51) Int. Cl.
C07C 7/12 (2006.01)

(52) U.S. Cl. .................. 585/828; 585/820; 585/827; 585/826

(58) Field of Classification Search .............. 585/820, 585/826, 827, 828
See application file for complete search history.

(56) References Cited

U.S. PATENT DOCUMENTS

| | | | |
|---|---|---|---|
| 3,201,491 A | 8/1965 | Stine et al. ............... 260/676 |
| 5,750,820 A | 5/1998 | Wei .......................... 585/826 |
| 5,884,777 A | 3/1999 | Pan et al. ................. 210/672 |
| 5,912,395 A | 6/1999 | Noe .......................... 585/820 |
| 6,004,518 A | 12/1999 | Green ....................... 422/190 |
| 6,149,874 A | 11/2000 | Hotier ...................... 422/142 |

FOREIGN PATENT DOCUMENTS

EP 1 060 776 A1 12/2000

*Primary Examiner*—Tam M. Nguyen
(74) *Attorney, Agent, or Firm*—David J Piasecki

(57) ABSTRACT

Product purity from or capacity of a simulated-moving-bed adsorptive separation process is increased by flushing the contents of the transfer line previously used to remove the raffinate stream away from the adsorbent chamber, preferably into the raffinate column used to separate desorbent from raffinate product. Preferably a stream from the adsorbent chamber at an intermediate point between the feed entry point and raffinate withdrawal is used as the flushing liquid. This flush step eliminates the passage of a quantity of the raffinate material into the adsorbent chamber in the transfer-line flush period or when the process conduit is subsequently used to charge the feed stream to the adsorbent chamber.

20 Claims, 1 Drawing Sheet

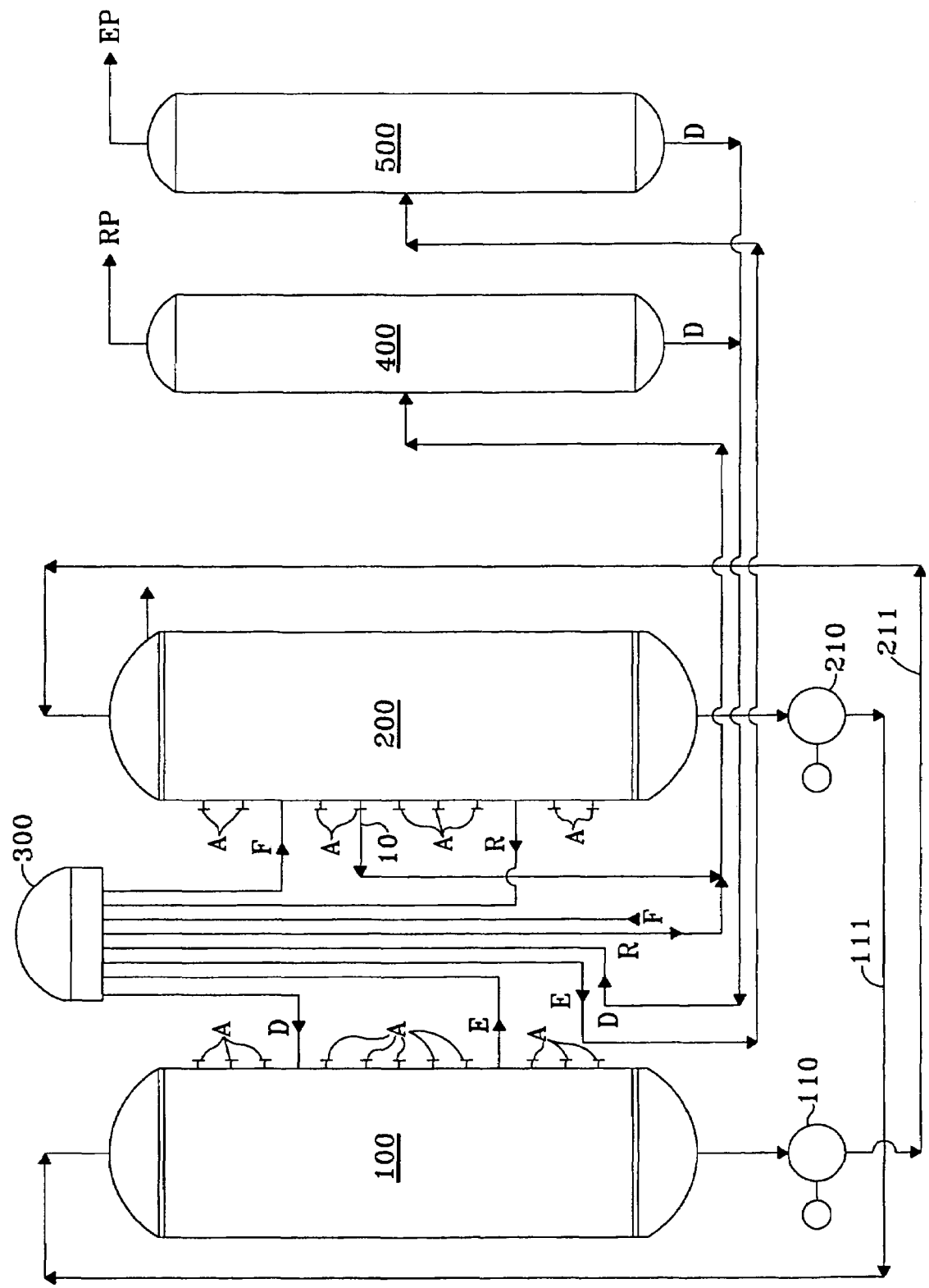

US 7,208,651 B2

PRODUCT RECOVERY FROM SIMULATED-MOVING-BED ADSORPTION

FIELD OF THE INVENTION

The subject invention relates to a process for the separation of hydrocarbons. More specifically, the invention relates to a process for the continuous simulated countercurrent adsorptive separation of aromatic hydrocarbons.

BACKGROUND OF THE INVENTION

Para-xylene and meta-xylene are important raw materials in the chemical and fiber industries. Terephthalic acid derived from para-xylene is used to produce polyester fabrics and other articles which are in wide use today. Meta-xylene is a raw material for the manufacture of a number of useful products including insecticides and isophthalic acid. One or a combination of adsorptive separation, crystallization and fractional distillation have been used to obtain these xylene isomers, with adsorptive separation capturing a great majority of the market share of newly constructed plants for the dominant para-xylene isomer.

Processes for adsorptive separation are widely described in the literature. For example, a general description directed to the recovery of para-xylene was presented at page 70 of the September 1970 edition of *Chemical Engineering Progress* (Vol. 66, No 9). There is a long history of available references describing useful adsorbents and desorbents, mechanical parts of a simulated moving-bed system including rotary valves for distributing liquid flows, the internals of the adsorbent chambers and control systems. The principle of using a simulated moving bed to continuously separate the components of a fluid mixture by contact with a solid adsorbent is as set forth in U.S. Pat. No. 2,985,589. U.S. Pat. No. 3,997,620 applies the principle of the simulated moving bed to the recovery of para-xylene from a feed stream containing $C_8$ aromatics, and U.S. Pat. No. 4,326,092 teaches meta-xylene recovery from a $C_8$-aromatics stream.

Adsorptive separation units processing $C_8$ aromatics generally use a simulated countercurrent movement of the adsorbent and the feed stream. This simulation is performed using established commercial technology wherein the adsorbent is held in place in one or more cylindrical adsorbent chambers and the positions at which the streams involved in the process enter and leave the chambers are slowly shifted along the length of the beds. Normally there are at least four streams (feed, desorbent, extract and raffinate) employed in this procedure and the location at which the feed and desorbent streams enter the chamber and the extract and raffinate streams leave the chamber are simultaneously shifted in the same direction at set intervals. Each shift in location of the transfer points delivers or removes liquid from a different bed within the chamber. The lines at these transfer points are reused as each stream enters or leaves the associated bed, and each line therefore carries one of the four process streams at some point in the cycle.

The art recognizes that the presence of residual compounds in the transfer lines can have detrimental effects on a simulated-moving-bed process. U.S. Pat. Nos. 3,201,491; 5,750,820; 5,884,777; 6,004,518; and 6,149,874 teach the flushing of the line used to deliver the feed stream to the adsorbent chamber as a means to increase the purity of the recovered extract or sorbate component. Such flushing avoids contamination of the extract stream with raffinate components of the feed remaining in this line when it is subsequently used to withdraw the extract stream from the chamber. U.S. Pat. No. 5,912,395 teaches flushing of the line just used to remove the raffinate stream in order to avoid contaminating feed with raffinate when this line is used to deliver the feed stream to the adsorbent chamber. All of these references teach flushing such lines back into the adsorbent chamber, thus increasing the separation load within the chamber.

SUMMARY OF THE INVENTION

A broad embodiment of the invention is a process for the separation of a desired compound from a feed mixture comprising two or more chemical compounds by simulated countercurrent adsorptive separation wherein a feed stream and a desorbent stream are injected into at least one multi-bed adsorbent chamber comprising a plurality of access points at two different access points via different transfer lines and an extract stream comprising the desired compound and a raffinate stream are individually withdrawn from the adsorbent chamber at two different access points by two additional transfer lines, the portion of the adsorption chamber between withdrawal of the raffinate and the injection of the feed stream being defined as an adsorption zone, the improvement which comprises directing one or both of a portion of the feed mixture and material withdrawn from the adsorption zone as a raffinate flush to flush away from the adsorbent chamber the contents of a transfer line which previously has been used to remove the raffinate stream from the adsorbent chamber.

A more specific embodiment of the invention is a process for the separation of a desired compound from a feed mixture comprising two or more chemical compounds by simulated countercurrent adsorptive separation wherein a feed stream and a desorbent stream are injected into at least one multi-bed adsorbent chamber comprising a plurality of access points at two different access points via different transfer lines and an extract stream comprising the desired compound and a raffinate stream are individually withdrawn from the adsorbent chamber at two different access points by two additional transfer lines and passed respectively to extract and raffinate distillation columns for recovery respectively of extract product and of raffinate product, the portion of the adsorption chamber between withdrawal of the raffinate and the injection of the feed stream being defined as an adsorption zone, the improvement which comprises directing one or both of a portion of the feed mixture and material withdrawn from the adsorption zone as a raffinate flush to flush to the raffinate column the contents of a transfer line which previously has been used to remove the raffinate stream from the adsorbent chamber.

A yet more specific embodiment is a process for the separation of a desired xylene isomer from a mixed $C_8$-aromatics feed stream by simulated countercurrent adsorptive separation wherein the feed stream and a desorbent stream are injected into at least one multi-bed adsorbent chamber comprising a plurality of access points at two different access points via different transfer lines and an extract stream comprising the desired xylene isomer and a raffinate stream are individually withdrawn from the adsorbent chamber at two different access points by two additional transfer lines and passed respectively to extract and raffinate distillation columns for recovery respectively of the desired xylene isomer and of raffinate product, the portion of the adsorption chamber between withdrawal of the raffinate and the injection of the feed stream being defined as an adsorption zone, the improvement which directing one or both of a portion of the feed mixture and material withdrawn from the adsorption zone as a raffinate flush to flush to the raffinate column the contents of a transfer line which previously has been used to remove the raffinate stream from the adsorbent chamber.

BRIEF DESCRIPTION OF THE DRAWING

The drawing is a simplified illustration of simulated-moving-bed adsorption showing features necessary to understand the invention.

DETAILED DESCRIPTION AND PREFERRED EMBODIMENTS

Adsorptive separation is applied to the recovery of a variety of hydrocarbon and other chemical products. Chemical separations using this approach which have been disclosed include the separation of mixtures of aromatics into specific aromatic isomers, of linear from nonlinear aliphatic and olefinic hydrocarbons, of either paraffins or aromatics from a feed mixture comprising both aromatics and paraffins, of chiral compounds for use in pharmaceuticals and fine chemicals, of oxygenates such as alcohols and ethers, and of carbohydrates such as sugars. Aromatics separations include mixtures of dialkyl-substituted monocyclic aromatics and of dimethyl naphthalenes. A major commercial application, which forms the focus of the prior references and of the following description of the present invention without so limiting it, is the recovery of para-xylene and/or meta-xylene from mixtures of $C_8$ aromatics. Such $C_8$ aromatics usually are derived within an aromatics complex by the catalytic reforming of naphtha followed by extraction and fractionation, or by transalkylation or isomerization of aromatics-rich streams in such complexes; the $C_8$ aromatics generally comprise a mixture of xylene isomers and ethylbenzene. Processing of $C_8$ aromatics simulated-moving-bed adsorption generally is directed to the recovery of high-purity para-xylene or high-purity meta-xylene; high purity usually is defined as at least 99.5 wt.-% of the desired product, and preferably at least 99.7 wt.-%.

The invention normally is employed in an adsorptive separation process which simulates countercurrent movement of the adsorbent and surrounding liquid as described above, but it may also be practiced in a cocurrent continuous process, like that disclosed in U.S. Pat. Nos. 4,402,832 and 4,478,721. The functions and properties of adsorbents and desorbents in the chromatographic separation of liquid components are well-known, and reference may be made to U.S. Pat. No. 4,642,397, which is incorporated herein, for additional description of these adsorption fundamentals. Countercurrent moving-bed or simulated-moving-bed countercurrent flow systems have a much greater separation efficiency for such separations than fixed-bed systems, as adsorption and desorption operations are continuously taking place with a continuous feed stream and continuous production of extract and raffinate. A thorough explanation of simulated-moving-bed processes is given in the Adsorptive Separation section of the Kirk-Othmer Encyclopedia of Chemical Technology at page 563.

The drawing is a schematic diagram of a simulated-moving-bed adsorption process employing the present invention. The process sequentially contacts a feed stream "F" with adsorbent contained in the vessels and a desorbent "D" to separate an extract stream "E" from a raffinate stream "R". In the simulated-moving-bed countercurrent flow system, progressive shifting of multiple liquid feed and product access points down an adsorbent chamber simulate the upward movement of adsorbent contained in the chamber. The adsorbent in a simulated-moving-bed adsorption process is contained in multiple beds in one or more vessels; two vessels 100 and 200 in series are shown in the drawing. Each vessel contains multiple beds of adsorbent in processing spaces 101 and 201, respectively. Each of the vessels has a number of access points relating to the number of beds of adsorbent, and the position of the feed stream F, desorbent input D, extract stream E and raffinate stream R are shifted along the access points to simulate a moving adsorbent bed. Circulating liquid comprising desorbent, extract and raffinate circulates through the vessels through pumps 110 and 210, respectively. Systems to control the flow of circulating liquid are described in U.S. Pat. No. 5,595,665, but the particulars of such systems are not essential to the present invention. A rotary disc type valve 300, as characterized for example in U.S. Pat. Nos. 3,040,777 and 3,422,848, effects the shifting of the streams along the adsorbent chamber to simulate countercurrent flow.

The various streams involved in simulated-moving-bed adsorption as illustrated in the drawing may be characterized as follows. A "feed stream" is a mixture containing one or more extract components and one or more raffinate components to be separated by the process. The "extract stream" comprises a component, usually the desired product, which is more selectively adsorbed by the adsorbent. The "raffinate stream" comprises components which are less selectively adsorbed. "Desorbent" refers to a material capable of desorbing an extract component, which generally is inert to the components of the feed stream and easily separable from both the extract and the raffinate.

The extract stream E and raffinate stream R from the illustrated scheme contain desorbent in concentrations relative to the respective product from the process of between 0% and 100%. The desorbent generally is separated from raffinate and extract components by conventional fractionation in raffinate column 400 and extract column 500 as illustrated in the drawing and returned to the process in stream D. The drawing shows the desorbent as bottoms from the respective column, implying that the desorbent is heavier than the extract or raffinate; different commercial units for the separation of $C_8$ aromatics employ either light or heavy desorbents. The raffinate product RP and extract product EP from the process are recovered from the extract stream E and the raffinate stream R in the respective columns; the extract product from the separation of $C_8$ aromatics usually comprises principally one or both of para-xylene and meta-xylene, with the raffinate being principally non-adsorbed $C_8$ aromatics and ethylbenzene.

The active liquid access points A effectively divide the adsorbent chamber into separate zones which move as the access points are shifted. The adsorption zone is located between the feed inlet stream F and the raffinate outlet stream R. In this zone, the feedstock contacts the adsorbent, an extract component is adsorbed, and a raffinate stream is withdrawn. Immediately upstream with respect to fluid flow is the purification zone, defined as the adsorbent between the extract outlet stream E and the feed inlet stream F. In the purification zone, the raffinate component is displaced from the nonselective void volume of the adsorbent and desorbed from the pore volume or surface of adsorbent shifting into this zone by passing a portion of extract stream material leaving the desorption zone. The desorption zone, upstream of the purification zone, is defined as the adsorbent between the desorbent inlet D and the extract stream outlet E. The desorbent passing into this zone displaces the extract component which was adsorbed by previous contact with feed in the adsorption zone. A buffer zone between the raffinate outlet stream R and the desorbent inlet stream D conserves the amount of desorbent utilized in the desorption step, in that a portion of the raffinate stream enters the buffer zone to displace desorbent material present in that zone into the desorption zone. The buffer zone contains enough adsorbent to prevent raffinate components from passing into the desorption zone and contaminating the extract stream.

Each of the zones described above generally are effected through multiple compartments or "beds" as described in U.S. Pat. No. 2,985,589. The positions of the various streams described are structurally separated from one another by a horizontal liquid collection/distribution grid. Each grid is connected to a transfer line defining a transfer point at which process streams enter and leave the adsorbent chamber. This arrangement facilitates the distribution of fluids within the chamber through eliminating channeling and other inefficiencies, prevents convective back-mixing of fluid in a direction opposite to that of primary fluid flow, and prevents migration of adsorbent through the chamber. Each of the zones described above usually comprises a plurality of 2 to 10, and more usually 3 to 8, beds. A typical simulated-moving-bed adsorption unit comprises 24 beds of adsorbent.

It is readily apparent that when a transfer line at an access point A which is being used to transport a particular stream into or out of the adsorbent chamber is left idle at the end of a step it will remain full of the compounds forming that stream until these compounds are removed from the line by a second flowing stream. The residual compounds left in the now unused transfer line will therefore be either withdrawn from the process as the initial part of a process stream removed from the process or forced into the adsorbent chamber when the transfer line carries a stream removed from or passed into the adsorbent chamber. As described above, those working in this art have recognized that the presence of these residual compounds in the transfer lines which previously have been used to remove the raffinate stream from the adsorbent chamber can have some detrimental effects on the performance of a simulated-moving-bed adsorptive separation process.

All of the prior references mentioned above teach flushing such lines which previously have been used to remove the raffinate stream from the adsorbent chamber back into the adsorbent chamber, thus increasing the separation load within the chamber. Resulting passage of desorbent into the adsorbent chamber is undesirable as the desorbent competes with the desired isomer for adsorptive sites on the adsorbent. The two compounds compete for the adsorptive capacity. A simplified summary of this is that the adsorption capacity of the adsorbent in the adsorption zone is the sum of the desired isomer and the desorbent compound which is adsorbed on the adsorbent. Decreasing the amount of desorbent charged to the adsorption zone therefore increases the amount of adsorbent capacity available for para-xylene or any other desired compound.

In contrast, the present invention teaches flushing away from the adsorbent chamber the contents of a transfer line which previously has been used to remove the raffinate stream from the adsorbent chamber, using a raffinate flush which thereafter preferably is directed the flush to the raffinate column. The raffinate flush may be one or both of the feed mixture and material withdrawn from the adsorption zone. This is illustrated in the drawing as line 10 from the adsorption zone which joins the raffinate R as feed to the raffinate column 400. The particular line 10 indicated on the drawing is not intended to limit the invention, as the flush material can be withdrawn from any point within the adsorption zone to flush a line at any access point within this zone. Preferably the flush material from the transfer line which had just previously carried the raffinate stream is flushed at an access point within two access points of the transfer line used for injection of the feed stream to the adsorbent chamber, in order to minimize the amount of desorbent remaining in the line when the feed stream is injected through this line. In comparison to processes of the known art, by directing the content of the line being flushed to the raffinate column, the capacity of the adsorbent chamber is not affected. Preferably the volume of the stream used to flush the raffinate transfer line is equal to from about 0.5 to about 2.5 times, more preferably from about 0.5 to 1.5 times, and optimally from about 0.9 to 1.1 times, of the total volume of the raffinate transfer line and associated valving. The associated valving refers to the valves and related appurtenances connected to the transfer line.

The practice of the subject invention requires no significant changes in operating conditions, adsorbent or desorbent composition or mechanical changes in the adsorbent chambers. The only significant required change to the process equipment is that needed to deliver a controlled quantity of one or both of the feed stream and an intermediate stream from the adsorption section of the process as a raffinate flush to the line to be flushed and connecting this line to the raffinate column. These changes are preferably made in and near the equipment used to control the flow of the process streams; thus, the subject process may be implemented on an existing unit by a modification in the equipment which directs fluid flow.

In selecting an adsorbent for the present simulated-moving-bed process, the only limitation is the effectiveness of the particular adsorbent/desorbent combination in the desired separation. An important characteristic of an adsorbent is the rate of exchange of the desorbent for the extract component of the feed mixture materials or, in other words, the relative rate of desorption of the extract component. This characteristic relates directly to the amount of desorbent material that must be employed in the process to recover the extract component from the adsorbent. Faster rates of exchange reduce the amount of desorbent material needed to remove the extract component, and therefore, permit a reduction in the operating cost of the process. With faster rates of exchange, less desorbent material has to be pumped through the process and separated from the extract stream for reuse in the process.

The practice of the subject invention thus is not related to or limited to the use of any particular adsorbent or adsorbent/desorbent combination, as differing sieve/desorbent combinations are used for different separations. The adsorbent may or may not be a zeolite. Examples of adsorbents which may be used in the process of this invention include nonzeolitic molecular sieves including carbon-based molecular sieves, silicalite and the crystalline aluminosilicates molecular sieves classified as X and Y zeolites. Details on the composition and synthesis of many of these microporous molecular sieves are provided in U.S. Pat. No. 4,793,984, which is incorporated herein for this teaching. Information on adsorbents may also be obtained from U.S. Pat. Nos. 4,385,994; 4,605,492; 4,310,440; and 4,440,871.

In adsorptive separation processes, which generally are operated continuously at substantially constant pressures and temperatures to insure liquid phase, the desorbent material must be selected to satisfy several criteria. First, the desorbent material should displace an extract component from the adsorbent with reasonable mass flow rates without itself being so strongly adsorbed as to unduly prevent an extract component from displacing the desorbent material in a following adsorption cycle. Expressed in terms of the selectivity, it is preferred that the adsorbent be more selective for all of the extract components with respect to a raffinate component than it is for the desorbent material with respect to a raffinate component. Secondly, desorbent materials must be compatible with the particular adsorbent and the particular feed mixture. More specifically, they must not reduce or destroy the capacity of the adsorbent or selectivity of the adsorbent for an extract component with respect to a raffinate component. Additionally, desorbent materials should not chemically react with or cause a chemical reaction of either an extract component or a raffinate component. Both the extract stream and the raffinate stream are typically removed from the adsorbent void volume in admixture with desorbent material and any chemical reaction involving a desorbent material and an extract component or a raffinate component or both would complicate or prevent product recovery. The desorbent should also be easily separated from the extract and raffinate components, as by fractionation. Finally, desorbent materials should be readily available and reasonable in cost. Benzene, toluene, and p-diethylbenzene are described as suitable desorbents for para-xylene recovery in the references, with p-diethylbenzene (p-DEB) having become a commercial standard for the separation. P-DEB is a "heavy" desorbent (higher boiling than para-xylene) which allows for easier recovery of the desorbent from the extract and raffinate streams by fractional distillation.

Adsorption conditions in general include a temperature range of from about 20° to about 250° C., with from about 60° to about 200° C. being preferred for para-xylene separation. Adsorption conditions also include a pressure sufficient to maintain liquid phase, which may be from about atmospheric to 4.2 MPa. Desorption conditions generally include the same range of temperatures and pressure as used for adsorption conditions. Different conditions may be preferred for other extract compounds.

EXAMPLES

In order to verify the improvement expected from the invention, a comparison was performed for the recovery of meta-xylene and of para-xylene from $C_8$ aromatics using a computerized model which has been shown to accurately predict and correlate with the actual operation of commercial scale simulated-moving-bed adsorptive separation units used to recover meta-xylene and of para-xylene from a mixture of xylene isomers. The simulated unit had twenty-four beds of adsorbent divided between two columns and a twenty-four port rotary valve to direct the flow of the process streams. Feedstock compositions were as follows in wt.-% for the two product targets:

|  | Meta-xylene | Para-xylene |
| --- | --- | --- |
| Toluene | 0.01 | 0.33 |
| Ethylbenzene | 24.03 | 9.35 |
| Para-xylene | 2.01 | 21.68 |
| Meta-xylene | 64.78 | 50.03 |
| Ortho-xylene | 8.31 | 16.91 |
| Non-aromatics | 0.86 | 1.70 |

Results were as follows, adjusting the relative amount of feed when effecting raffinate flush away from the chamber to normalize product purity/recovery:

| Meta-xylene recovery: | | | | |
| --- | --- | --- | --- | --- |
| Case | Description | Feed Rate | Purity | Recovery |
| Base | No raffinate flush | Base | 99.66% | 89.65% |
| Invention | Raffinate flush from chamber | Base | 99.64% | 99.52% |
| Invention | Raffinate flush from chamber | 1.4 × Base | 99.64% | 99.48% |
| Known art | Raffinate flush to chamber | Base | 99.64% | 99.56% |
| Known art | Raffinate flush to chamber | 1.4 × Base | 99.64% | 91.43% |

| Para-xylene recovery: | | | | |
| --- | --- | --- | --- | --- |
| Case | Description | Feed Rate | Purity | Recovery |
| Base | No raffinate flush | Base | 99.72% | 96.80% |
| Invention | Raffinate flush from chamber | Base | 99.75% | 98.59% |
| Invention | Raffinate flush from chamber | 1.1 × Base | 99.73% | 96.97% |

The resulting increase in capacity was about 40% when recovering meta-xylene and about 10% when recovering para-xylene. Note that recovery was not maintained when the raffinate flush was directed to the chamber.

The above description and examples are intended to be illustrative of the invention without limiting its scope. The skilled routineer will readily understand how to extrapolate parameters of the disclosure to other embodiments of the invention. The invention is limited only by the claims set forth herein.

I claim:

1. In a process for the separation of a desired compound from a feed mixture comprising two or more chemical compounds by simulated countercurrent adsorptive separation wherein a feed stream and a desorbent stream are injected into at least one multi-bed adsorbent chamber comprising a plurality of access points at two different access points via different transfer lines and an extract stream comprising the desired compound and a raffinate stream are individually withdrawn from the adsorbent chamber at two different access points by two additional transfer lines, the portion of the adsorption chamber between withdrawal of the raffinate and the injection of the feed stream being defined as an adsorption zone, the improvement which comprises directing one or both of a portion of the feed mixture and material withdrawn from the adsorption zone as a raffinate flush to flush away from the adsorbent chamber the contents of a transfer line which previously has been used to remove the raffinate stream from the adsorbent chamber, and passing the contents of the transfer line being flushed with the raffinate flush to a raffinate distillation column.

2. The process of claim 1 further characterized in that the raffinate flush from the transfer line which had just previously carried the raffinate stream is flushed at an access point within two access points of the transfer line being used for injection of the feed stream to the adsorbent chamber.

3. The process of claim 1 wherein the volume of the raffinate flush is from about 0.5 to about 2.5 times the total volume of the raffinate transfer line and associated valving.

4. The process of claim 1 wherein the volume of the raffinate flush is from about 0.5 to about 1.5 times the total volume of the raffinate transfer line and associated valving.

5. The process of claim 1 wherein the volume of the raffinate flush is from about 0.9 to about 1.1 times the total volume of the raffinate transfer line and associated valving.

6. The process of claim 1 wherein the feed stream comprises $C_8$ aromatics and an extract product comprises high-purity meta-xylene.

7. The process of claim 1 wherein the feed stream comprises $C_8$ aromatics and an extract product comprises high-purity para-xylene.

8. The process of claim 1 wherein the feed stream comprises one or more nonlinear aliphatic and olefinic hydrocarbons.

9. The process of claim 1 wherein the feed stream comprises a feed mixture comprising both aromatics and paraffins.

10. The process of claim 1 wherein the feed stream comprises chiral compounds for use in pharmaceuticals and fine chemicals.

11. The process of claim 1 wherein the feed stream comprises one or more alcohols and ethers.

12. The process of claim 1 wherein the feed stream comprises one of the group consisting of carbohydrates, sugars, and combinations thereof.

13. In a process for the separation of a desired compound from a feed mixture comprising two or more chemical compounds by simulated countercurrent adsorptive separation wherein a feed stream and a desorbent stream are injected into at least one multi-bed adsorbent chamber comprising a plurality of access points at two different access points via different transfer lines and an extract stream comprising the desired compound and a raffinate stream are individually withdrawn from the adsorbent chamber at two different access points by two additional transfer lines and passed respectively to extract and raffinate distillation columns for recovery respectively of extract product and of raffinate product, the portion of the adsorption chamber between withdrawal of the raffinate and the injection of the feed stream being defined as an adsorption zone, the improvement which comprises directing one or both of a portion of the feed mixture and material withdrawn from the adsorption zone as a raffinate flush to flush to the raffinate column the contents of a transfer line which previously has been used to remove the raffinate stream from the adsorbent chamber.

14. The process of claim 13 wherein the volume of the raffinate flush is from about 0.5 to about 2.5 times the total volume of the raffinate transfer line and associated valving.

15. The process of claim 13 wherein the volume of the raffinate flush is from about 0.5 to about 1.5 times the total volume of the raffinate transfer line and associated valving.

16. The process of claim 13 wherein the volume of the raffinate flush is from about 0.9 to about 1.1 times the total volume of the raffinate transfer line and associated valving.

17. In a process for the separation of a desired xylene isomer from a mixed $C_8$-aromatics feed stream by simulated countercurrent adsorptive separation wherein the feed stream and a desorbent stream are injected into at least one multi-bed adsorbent chamber comprising a plurality of access points at two different access points via different transfer lines and an extract stream comprising the desired xylene isomer and a raffinate stream are individually withdrawn from the adsorbent chamber at two different access points by two additional transfer lines and passed respectively to extract and raffinate distillation columns for recovery respectively of one or both of the desired xylene isomer and of raffinate product, the portion of the adsorption chamber between withdrawal of the raffinate and the injection of the feed stream being defined as an adsorption zone, the improvement comprising directing one or both of a portion of the feed mixture and material withdrawn from the adsorption zone as a raffinate flush to flush to the raffinate column the contents of a transfer line which previously has been used to remove the raffinate stream from the adsorbent chamber.

18. The process of claim 17 wherein the desired xylene isomer comprises one or both of high-purity meta-xylene and high-purity para-xylene.

19. The process of claim 18 wherein the desired xylene isomer consists essentially of high-purity meta-xylene.

20. The process of claim 18 wherein the desired xylene isomer consists essentially of high-purity para-xylene.

* * * * *